US00PP09046P

United States Patent [19]

Bubani

[11] Patent Number: Plant 9,046

[45] Date of Patent: Jan. 24, 1995

[54] NECTARINE TREE KNOWN AS LAURA

[76] Inventor: Giovanni B. Bubani, 921 N. Peach Ave., No. 119, Fresno, Calif. 93727-2492

[21] Appl. No.: 169,000

[22] Filed: Dec. 20, 1993

[51] Int. Cl.[6] ..... A01H 5/00
[52] U.S. Cl. ..... Plt./41.1
[58] Field of Search ..... Plt. 41.1

[56] References Cited

PUBLICATIONS (The Society) (Listing for) 'Nina', *Proceedings of the American Pomological Society*, Columbus, Ohio, 1922 page unknown.

Hedrick, U. P. (Listings for) 'Laura'; 'Laura Cling', *The Peaches of New York*, 1917, Geneva Ag. Exper. Sta., Bull. Rept., 1916, Pt. II., p. 401.

Childers, N. T., "Scientific Names of Some Deciduous Fruits" *Fruit Science*, 4th Ed., 1969, p. 833.

*Primary Examiner*—James R. Feyrer
*Attorney, Agent, or Firm*—Dennis B. Haase

[57] ABSTRACT

A new and distinct variety of nectarine tree bearing fruit which is large and has yellow-gold flesh, and which matures in the early in the season, while having an excellent balance of sugar and acidity, the size of the fruit being large with skin of a red blush color ranging from dark garnet red to a lighter red with numerous yellow dots make it very attractive in appearance and flesh of a firm and crisp texture, becoming juicy with after ripening, making it very tasty to eat.

1 Drawing Sheet

BACKGROUND OF THE NEW VARIETY

The present invention relates to a new and distinct variety of nectarine tree, which I refer to as "Laura", of a yellow-gold fleshed, large size, semi-cling stone fruit, attractive in appearance, maturing in the early season period, which was developed as part of a continuing fruit breeding program being conducted in the San Joaquin Valley of California. Applicant has carried on a variety improvement program in California for over ten years and during that period has evaluated over 10,000 individual seedlings of various species. Seedlings that have sprouted in various orchard locations within the San Joaquin Valley are routinely collected and are either transplanted from the orchard floor to a seedling block and/or grafted onto rootstock for eventual evaluation of the fruit. Routine inspections of the orchard plantings are made for any mutations which might arise having superior characteristics over the parent.

ORIGIN AND ASEXUAL REPRODUCTION OF THE NEW VARIETY

The seedling of the subject nectarine variety was found growing in an orchard of the "Early Sun Grand" nectarine variety, where it had sprouted after having been incorporated in the soil by fall discing of the orchard floor. In the spring, the seedlings derived from those sprouts were embodied as part of the aforesaid ongoing breeding program by grafting first to Nemaguard rootstock in Fresno County, Calif., and later several others were grafted to a French rootstock known as G-F 677 in Exeter, Calif. Both grafts produced plant material which is the subject of this application.

SUMMARY OF THE NEW VARIETY

The new variety can be characterized as an early maturing, large size nectarine, which exhibits superior fruit coloration and edibility when compared with other commercial nectarines ripening in its season.

A comparison can be drawn between the new variety and the May Grand (U.S. Plant Pat. No. 2,794) nectarine variety which has been one of the most prominent early season nectarine varieties grown in California. The new variety is early ripening with first pick on or about Jun. 4, 1993, a few days ahead of May Grand, which usually ripens at the end of the first week of June (Jun. 7, 1993 in the Sanger area of the San Joaquin Valley of California). The new variety, however, has substantially larger fruit size than the May Grand, which often produces many smaller sized fruit. In addition, the new variety has superior color, which is more eye appealing when compared to May Grand in that the new variety has both a higher percentage of red coloring about the fruit's surface and the red coloring is a darker and more glossy than its competitor.

Unlike the May Grand variety which requires large number of hours of cold temperatures, the present variety requires significantly fewer hours of cold temperatures. As a consequence, while the May Grand will often produce a light fruit set in warmer winters and, therefore, a greatly reduced crop, the present variety will produce a greater crop of acceptable fruit irrespective of winter temperatures. Moreover, whereas the May Grand is pruned to allow for much greater fruit wood to make up for an anticipated light crop, the present variety may be pruned to allow for increased fruit size, thereby enhancing marketability.

There are several other characteristics of the fruit which make the new variety a distinct and patentable improvement over the May Grand. While the flavor of the new variety is at least equal to the excellent flavor of the May Grand, the fruit of the new variety produces fewer external split pits and is less elongate in form than May Grand. Additionally, the apex of the new variety is depressed rather than having a tip as is the case with May Grand, making it less prone to damage during picking and handling. Considering all of the positive characteristics enumerated herein, the new variety displays a substantial degree of improvement and marketability over the May Grand.

BRIEF DESCRIPTION OF THE DRAWING

The accompanying drawing illustrates typical specimens of the fruit and foliage of my new variety as grown in the San Joaquin Valley of California. Two specimens are shown, one of which is in the side elevation and the other from the apex view; yet another specimen is a section side elevation illustrating the internal texture and color of the flesh and pit.

DETAILED DESCRIPTION

The following is a detailed description of my new variety. Color definitions listed in this description are from "Dictionary of Color" by Maerz and Paul, 1st Edition published in 1930.

TREE

Generally: Hardy.

*Size.*—Large (9.5 feet in width and 11.5 feet in height, developing from 3.5 to 5 feet of new growth in the top of the tree during the growing season), vigorous, spreading, open, vase form; not unusually large for nectarine trees and is, in fact, average for such trees grown on the rich alluvial soils found in the Sanger river bottom area of Fresno County, Calif.

*Scaffold branches.*—Trees of the new variety appears to be normal in structural strength, needing to be tied with tying twine in the upper portion of the three, but not normally needing to be propped. Scaffold angles range from upright to upright-spreading. The specimen tree described was propagated by fall budding in September of 1988 on rootstock that was at that time almost one year in age.

*Vigor.*—Vigorous, productive.

*Regularity of bearing.*—Regular bearer.

Trunk:

*Size.*—Medium thickness, from 3 to 3.3" in diameter.

*Surface texture.*—Average in comparison with other common commercial nectarine varieties.

*Bark.*—Relative smooth, with numerous large bank lenticels.

*Color.*—Grey-brown (150-C-8, Chukkar Brown).

*Lenticels.*—Lenticels are oval in form from 6 to 10 mm in length and from 2 to 3 mm in height.

Branches: Branches are of average thickness and relatively smooth in surface texture. The color of the mature branches is a medium brown (7-H-11, Casserole Brown); current season's growth is a pale green (18-J-3), often with a rose colored blush on exposed surfaces (3-L-10, Japan Rose). Color of the expanding shoot tips is a bright shiny green-yellow (18-L-2 Citronella Green); internode length is in the normal range, from 27 to 35 mm between nodes on current season's hanger wood.

Pollination: The new variety has been found to be self-pollinating by virtue of limb bagging tests performed by the Applicant during the 1987 blooming season.

LEAVES

Generally: Leaves are medium to large in size. Leaf measurements have been established from large leaves growing on vigorous, vertical, current season's shoots and are in the largest size ranges. Leaf length varies from 15.4 to 16.7 cm and leaf width from 3.7 to 4.3 cm. Leaf thickness appears normal.

*Form.*—General leaf from is lanceolate. Leaf tip form is acuminate. The leaf spices are often reflexed downwards and slightly twisted sideways.

*Color.*—The coloration of the upper leaf surface is a dark green (24-L-3); lower leaf surfaces are colored a lighter green (23-J-4, Lincoln Green). The large mid-vein on the lower leaf surface is colored a pale green-yellow (19-J-2).

*Margins.*—Margin form is intermediate in type, but most nearly serrate in form, especially apically. Margin form at mid-margin and basally are less strongly serrate, approaching crenate in form. Serrations are low and somewhat irregular; leaf margins are moderately undulate.

*Petiole.*—The petiole is medium in size, from 7 to 10 mm in length and from 1.5 to 2.0 mm in thickness. Petiole color is a pale green-yellow (19-J-2) on lower surfaces but a darker green on upper surfaces and within the petiole groove (21-J-3).

*Glands.*—Three to four glands are present usually on, or just below, the base of the leaf margin. These glands are variable but most frequently are stalked and globose in form, although reniform types can often be found. The glands are medium in size and alternate in position. Color of the new glands is a bright green (17-L-6), becoming dark with age.

*Stipules.*—Medium to large in size, from 9 to 14 mm in length; form is linear lanceolate with serrate margins. Color of the stipules is a light yellow-green (18-L-3) when young, but the stipules deteriorate, rapidly becoming red-orange in color (3-C-11), Burmese Gold) and are early deciduous.

FLOWERS

Floral buds: Dormant floral buds are medium in size and grey-brown in color (7-A-10New Cocoa). Bud from is conic and free from the bearing stem. The surface of the bud scales is pubescent. The buds are hardy under typical climatic conditions as found in the Central San Joaquin Valley.

Bloom timing:—Bloom is relatively early in relation to other commercial nectarine cultivars commonly grown in this production area; date of bloom was Mar. 3, 1993.

*Flower size.*—Flowers are of the small "nonshowy" category, and are mid-range within this category. Flower diameter, fully expanded ranges from 22 to 25 mm.

*Bloom abundance.*—Bloom quantity is abundant with 1 to 3 flower buds being present per node, but most frequently 2.

*Petal size.*—Petals are medium in size from 12 to 14 mm in length and from 7 to 9 mm in width.

*Petal form.*—Form is variable but most frequently the petals are obovate. Petal number is usually 5, but at times 5 or more additional small narrow petals can be present.

*Petal color.*—Color of the young petals is a pale pink (1-C-2 Peach Blossom) with darker rose margins (1-G-3), with blossom color usually becoming darker with age.

*Petal claw form.*—The petal claw is short, truncate and relatively broad, from 1 to 1.5 mm in width.

*Petal margins.*—The petal margins are undulate and usually substantially cupped inwards.

*Petal apex.*—Petal apices are generally rounded.

*Flower pedicel.*—Pedicel size is average; length ranges from 2 to 2.5 mm and thickness averages 1 mm. Pedicel color is a bright shiny green (17-L-7 Viridine Green), overlaid with a small amount of maroon speckling (6-J-4). The pedicel surface is glabrous.

*Calyx.*—Calyx surface is glabrous with maroon (6-E-5) coloration, marked basally with longitudinal green striations (18-L-8, Eve Green).

*Sepals.*—Sepal surfaces are pubescent with moderately long grayish pubescence. The sepals are medium in size and broadly ovate in form. Sepal color is green (21-K-4 Rainette Green) with maroon specking (6-H-4).

*Floral nectarines.*—The nectaries are a bright orange in color (3-E-12 Burnt Orange), becoming slightly darker with age.

*Anthers.*—The anthers are average in size. Anther color is red dorsally (3-L-11, Blood Red) and chamois ventrally (11-H-6) often with red margins. Pollen in the anthers is abundant and golden-yellow in color (10-L-4, Light Chrome).

*Stamens.*—Stamens are variable in length from 12 to 16 mm, with the longest stamens being about equal in length to the pistil. Filament color is a light pink (1-B-1) becoming a darker rose color with age (2-H-4).

*Pistil.*—Pistil length ranges from 17 to 18 mm, including the ovary. Pistil color is a pale green (17-H-3) and the surface of the pistil is glabrous.

FRUIT

Maturity when described: In a firm ripe condition for commercial harvesting and shipment approximately June 4 to June 8 near Sanger in the central San Joaquin Valley of California.

Size:

*Generally.*—Uniform, large.

*Average diameter in the axial plane.*—From 68 to 71 mm.

*Average diameter transverse in the suture plane.*—From 66 to 72 mm.

*Average cheek diameter.*—From 64 to 72 mm.

*Form.*—Form is variable from slightly ovate to nearly globose in lateral aspect. In apical aspect, the fruit is oval and usually slightly asymmetrical.

Suture:

*Generally.*—A continuous line from base to apex, deepening and widening over the apical shoulder, more shallow basally. Occasionally the ventral suture is slightly folded within the stem cavity basin. A thin variable red suture stripe is often present, which expresses itself as a light red stirpes when the fruit is highly colored or sometimes as a darker red stripe when the underlying coloration is light. The suture stirpes is from 1.5 to 2 mm in width at mid-suture.

*Ventral surface.*—Relatively smooth, only very slightly lipped, usually apically.

*Stem cavity—generally.*—Medium in size and oval in form.

*Stem cavity—width.*—Ranges from 23 to 28 mm.

*Stem cavity—depth.*—Ranges from 11 to 14 mm.

*Stem cavity—length.*—Ranges from 27 to 32 mm.

*Fruit shoulders.*—An occasional groove is present in the cavity shoulder where the fruit was pressed next to the bearing limb.

*Fruit base.*—Usually moderately truncate in form with a variable base angle from very slightly oblique to at right angle to the fruit axis.

*Fruit apex.*—Typically substantially depressed, as much as 3 to 5 mm below the apical shoulders. The apical shoulders are rounded, and the pistil point is apical.

*Fruit stem.*—Medium in size.

*Fruit stem—length.*—Ranges from 8.5 to 10 mm.

*Fruit stem—thickness.*—Ranges from 2.5 to 3 mm.

*Fruit stem—color.*—Light grey-green (21-J-3) with varying amounts of brown present (14-H-6).

Skin:

*Thickness.*—Average thickness and tenacious to flesh at commercial maturity.

*Texture.*—Glabrous.

*Flavor.*—Slightly acidic.

*Tendency to crack.*—No tendency to crack has been observed.

*Color.*—Highly blushed with 60% to 90% of the fruit surface exhibiting some red coloration. The blush is usually present in a washed pattern, although some striping and dappling can be present. The red blush color ranges from a dark garnet red (6-L-6, Chianti Red) to a lighter red (4-K-11, Lacquer Red). Most of the fruit surface is quite glossy. Numerous light colored yellow dots can be present (10-L-2 Aureolin Yellow), most frequently over the apex and apical shoulders. Percentage of ground color present can range from 10% to 40% of the fruit surface.

*Ground color.*—Bright yellow (10-L-3).

*Flesh color.*—Light yellow-gold (9-K-3, Empire Yellow) and is quite uniform throughout. A medium number of light colored, tender fibers are present throughout the flesh. The flesh color near the pits is essentially the same as the overall interior fresh color, 9-K-3, Empire Yellow.

Texture.—The flesh is crisp and firm at commercial maturity and retains that texture throughout the harvest period, hanging well on the tree. After harvest and/or with advancing maturity, the flesh softens and becomes somewhat juicy, but only moderately so.

*Ripening.*—Ripens evenly.

*Flavor.*—Sweet and rich with an excellent balance of sugar and acidity.

*Aroma.*—Moderate in volume and pleasant in smell.

*Eating quality.*—Excellent.

Stone:

*Attachment.*—Semi-cling; tightly attached at commercial maturity, becoming semi-free with advancing maturity.

*Size.*—Medium to large.

*Length.*—Ranges from 37 to 41 mm.

*Thickness.*—Ranges from 20 to 25 mm.

*Width.*—Ranges from 28 to 30 mm.

*Fibers—numbers.*—Numerous; attached to the stone throughout, but more dense along both sutures, especially basally.

*Fibers—length.*—Medium length.

*Form.*—Variable, most frequently oval to occasionally obovate.

*Base.*—Slightly truncate with a variable base angle from very slightly oblique to a right angle to the fruit axis.

*Hilum.*—Moderately large in size and generally oval in form, but with irregular edges. The entire hilum area is substantially eroded.

*Apex.*—Acute in form.

*Sides.*—Variable, but most frequently are unequal in size.

*Surface.*—Quite coarse with relatively high ridges and deep pits laterally.

*Ventral edge.*—Wide, from 5 to 7.5 mm in thickness at mid-suture. The suture wings are relatively low and coalesced, converging apically with wings slightly more prominent basally, extending out 2.5 to 5 mm from the body of the stone.

*Dorsal edge.*—A deep and wide groove is present, extending from the stone base to within 7 to 10 mm of the apex. The groove is subtended by two prominent ridges, which in turn are notched in several places by cross grooves. The upper apical shoulder along the dorsal edge is substantially eroded from the upper extremity of the dorsal groove up to, and occasionally including, the apex.

*Color.*—The dry stone is a light tan (10-D-2).

*Tendency to split.*—A moderate number of internal split stones are present, but no external splits are in evidence.

Use: This new cultivar is an early ripening, fresh market nectarine with potential for use in both local market and long distance shipping.

Keeping quality: Excellent.

Shipping quality: Excellent.

Resistance to disease: Very good.

Although the new variety of nectarine tree possesses the described characteristics noted above as a result of the growing conditions prevailing near Sanger in the central part of the San Joaquin Valley of California, it is to be understood that variations of the usual magnitude and characteristics incident to changes in growing conditions, irrigation, fertilization, pruning and pest control are to be expected.

Having thus described and illustrated my new nectarine tree, what is claimed as new and desired to be secured by Letters Patent is:

1. A new and distinct variety of nectarine tree substantially as shown and described, and characterized by its early maturing fruit of large size and excellent sugar balance and, further, having firm, highly edible flesh and skin of a red blush color ranging from dark garnet red to a lighter red with numerous yellow dots, giving it a very attracive appearance, and flesh of a firm and crisp texture and becoming juicy with after ripening.

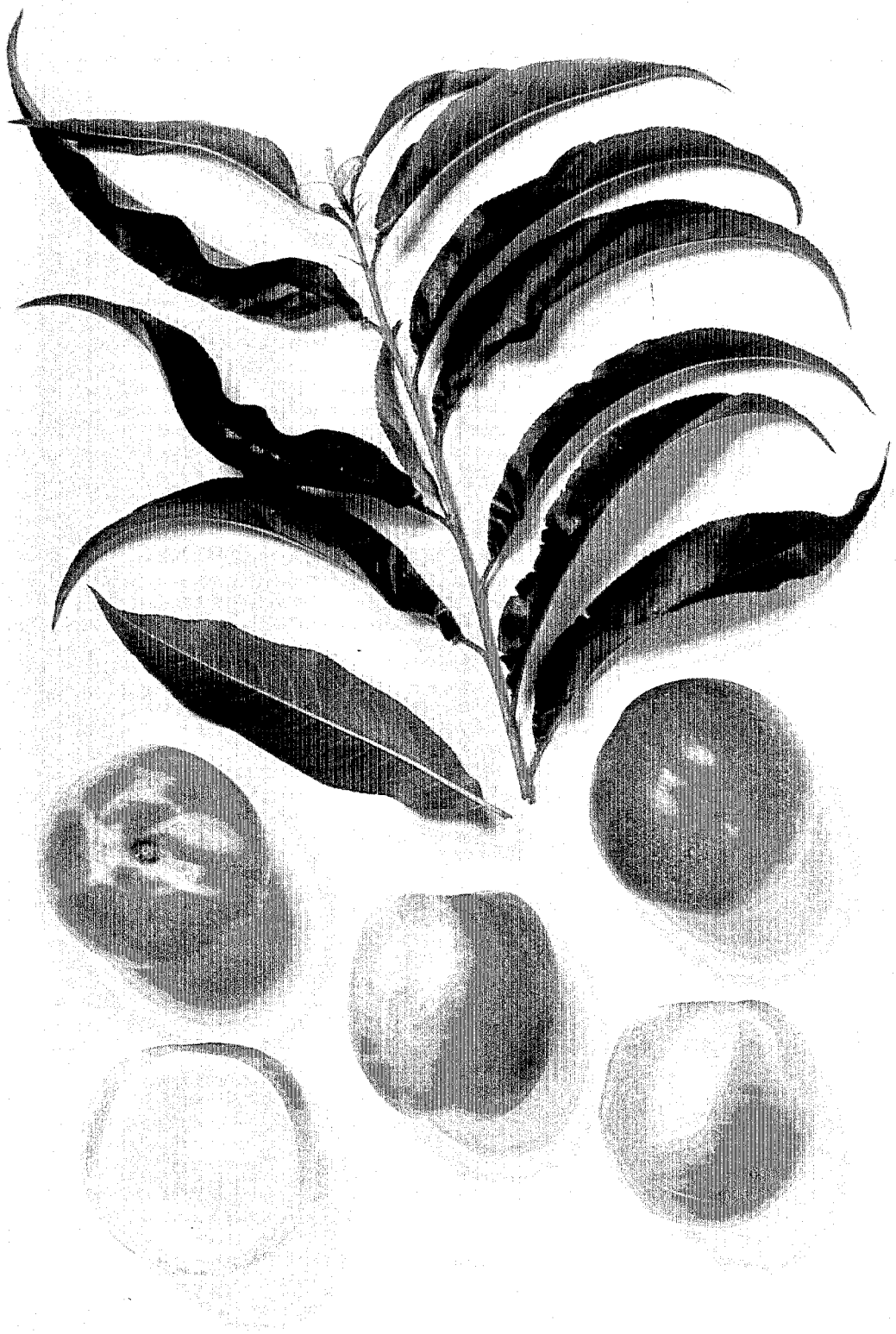

* * * * *